United States Patent
Cornman et al.

(10) Patent No.: US 11,399,967 B2
(45) Date of Patent: Aug. 2, 2022

(54) SYSTEM AND METHOD FOR A PROSTHETIC HAND HAVING SENSORED BRUSHLESS MOTORS

(71) Applicant: Psyonic, Inc., Champaign, IL (US)

(72) Inventors: Jesse Cornman, Champaign, IL (US); Aadeel Akhtar, Urbana, IL (US)

(73) Assignee: Psyonic, Inc., Champaign, IL (US)

( * ) Notice: Subject to any disclaimer, the term of this patent is extended or adjusted under 35 U.S.C. 154(b) by 180 days.

(21) Appl. No.: 16/834,970

(22) Filed: Mar. 30, 2020

(65) Prior Publication Data

US 2020/0306059 A1     Oct. 1, 2020

Related U.S. Application Data

(60) Provisional application No. 62/826,981, filed on Mar. 29, 2019.

(51) Int. Cl.

| | |
|---|---|
| A61F 2/54 | (2006.01) |
| A61F 2/70 | (2006.01) |
| B25J 9/12 | (2006.01) |
| B25J 15/10 | (2006.01) |
| A61F 2/68 | (2006.01) |
| A61F 2/58 | (2006.01) |
| B25J 15/00 | (2006.01) |

(52) U.S. Cl.
CPC .............. *A61F 2/68* (2013.01); *A61F 2/586* (2013.01); *B25J 9/126* (2013.01); *B25J 15/0009* (2013.01); *A61F 2002/587* (2013.01); *A61F 2002/6836* (2013.01); *A61F 2002/6863* (2013.01); *A61F 2002/701* (2013.01)

(58) Field of Classification Search
CPC .. A61F 2/586; A61F 2002/587; B25J 15/0009
USPC ...................................................... 623/63–64
See application file for complete search history.

(56) References Cited

U.S. PATENT DOCUMENTS

| | | |
|---|---|---|
| 2005/0021154 A1 | 1/2005 | Brimalm |
| 2010/0036507 A1 | 2/2010 | Gow |
| 2013/0053984 A1 | 2/2013 | Hunter et al. |
| 2015/0230941 A1 | 8/2015 | Jury |
| 2017/0007424 A1 | 1/2017 | Gill |
| 2017/0020691 A1 | 1/2017 | Thompson et al. |
| 2019/0328550 A1 | 10/2019 | Akhtar et al. |

*Primary Examiner* — David H Willse
(74) *Attorney, Agent, or Firm* — Alpine Patents LLC; Brian Van Osdol

(57) ABSTRACT

A system and method for a prosthetic assembly that includes a first prosthetic component, comprising a prosthetic hand base; a set of second prosthetic components, comprising a set of prosthetic fingers, and a set of actuating systems, wherein one actuating system connects a pair of distinct prosthetic components, enabling actuation of one prosthetic component with respect to the other. Each actuating system, from the set of actuating systems, includes a linkage and a sensored brushless motor; wherein the sensored brushless motor comprises a brushless motor, a field oriented control system, a rotary encoder, and a gearbox.

19 Claims, 12 Drawing Sheets

SYSTEM AND METHOD FOR A PROSTHETIC HAND HAVING SENSORED BRUSHLESS MOTORS

CROSS-REFERENCE TO RELATED APPLICATIONS

This Application claims the benefit of U.S. Provisional Application No. 62/826,981, filed on 29 Mar. 2019, which is incorporated in its entirety by this reference.

TECHNICAL FIELD

This invention relates generally to the field of prosthetics, and more specifically to a new and useful system and method for a prosthetic assembly having sensored brushless motors.

BACKGROUND

Nearly as long as humans have existed, human injuries and ailments have existed that have led to loss or lack of limb. As an ingenuous species, humans have constantly developed tools and prostheses to cope with these lost limbs. With human advancement these prostheses have improved and become closer in capability to the original lost limb.

With the development of myoelectric prosthetic devices, prostheses have reached a new level wherein human muscle signals could be used to control motors on or within a prosthetic limb. Myoelectric prostheses have enabled construction of complex prostheses that start to resemble intact limbs in functionality. Motors can now be incorporated into appropriately sized prosthetic limbs, enabling life-like functionality.

This development has reached a choke point in the field of prosthetics that has been limited by the ability and size of the motors implemented in prosthetic limbs. Small motors that could fit in a prosthetic limb are too weak, have slow reaction times, and have limited durability. Motors with sufficient power, fast reaction times, and high precision, have been too large to implement in multitude within a small prosthetic limb.

Thus, there is a need in the field of prosthetics to create a new and useful system and method for a prosthetic assembly containing a multitude of motors with sufficient power, precision, and durability. This invention provides such a new and useful system and method.

DESCRIPTION OF THE EMBODIMENTS

Figure 1:
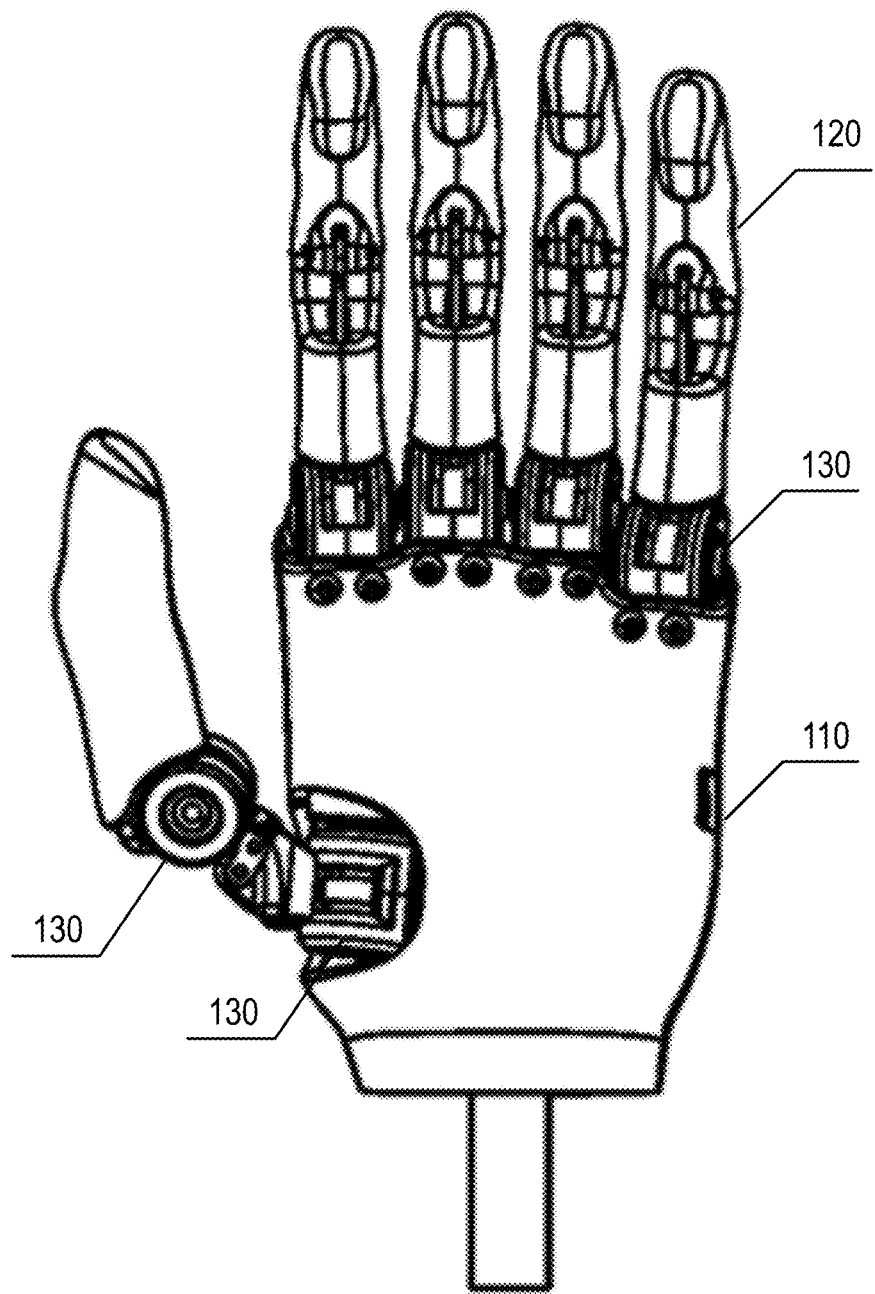
FIG. 1 is a schematic representation of a system of a preferred embodiment.

The following description of the embodiments of the invention is not intended to limit the invention to these embodiments but rather to enable a person skilled in the art to make and use this invention.

1. Overview

A system and method for an actuating system for a prosthetic assembly preferably utilizes sensored brushless motors for the actuation of a "moving" prosthetic component with respect to a "fixed" prosthetic component. The system and method are preferably applied to a prosthetic assembly of a prosthetic hand, wherein sensored brushless motors actuate prosthetic fingers with respect to a prosthetic hand base. The sensored brushless motors are preferably sufficiently miniaturized such that a plurality of sensored brushless motors may fit within the fixed prosthetic component (e.g. prosthetic and hand base) and generate sufficient locomotion to drive actuation of the "moving" prosthetic components (e.g. prosthetic fingers). The sensored brushless motors are preferably high precision Field Oriented Control (FOC) brushless motors that may be employed as backdrivable or non-backdrivable, as desired.

In preferred variations, the prosthetic assembly comprises a prosthetic hand, wherein the prosthetic hand has at least five degrees of motion (e.g., one for each finger, and two for the thumb). These degrees of motion are fixed by a 4-bar linkage system that enables actuation along the degrees of freedom. Sensored brushless motors in the hand base drive actuation, through field oriented control (FOC), of each connected prosthetic finger, enabling individual opening and closing of each finger of the prosthetic hand. Additionally, the system and method may employ additional sensored brushless motors to add degrees of motion. In one preferred variation, the prosthetic hand includes a sixth degree of motion through a second sensored brushless motor within the thumb of the prosthetic hand enabling both flexion and opposition/rotation of the thumb. FIGS. 4-7 show model representations of preferred embodiment of the prosthetic hand and prosthetic hand components.

The system and method preferably employ efficient control circuitry for control of the plurality of brushless motors. Preferably, a set of field oriented control circuits are implemented within a printed circuit board (PCB) housed in the palm of a hand base. Furthermore, the brushless motors preferably have physical/hardware calibrated encoders directly mounted that are pre-synchronized for collective use across the plurality of fingers of a prosthetic hand. Being calibrated pre-synchronized can make the individual motors pre-configured for use in a hand thereby being interchangeable and possibly not needing in-place software calibration.

The system and method may provide a number of potential benefits. The system and method are not limited to always providing such benefits, and are presented only as exemplary representations for how the system and method may be put to use. The list of benefits is not intended to be exhaustive and other benefits may additionally or alternatively exist.

As one potential benefit, the FOC sensored brushless motors of the system and method may give the system and method greater strength and efficiency in actuation. The improved strength may enable greater grip strength in a prosthetic hand (e.g. for grabbing objects) while the improved efficiency may reduce battery consumption.

Additionally, the innovative integration of FOC sensored brushless motors may give the system and method a high level of precision in actuation. The high level of precision enables better high-level coordinated actuation between multiple hand components to enable subtle mechanical changes for similar tasks (e.g. grabbing an egg or grabbing a ball).

As another potential added benefit, FOC sensored brushless motors can produce much less sound than other motors (e.g. brushed motors). This may enable the prosthetic assembly of this system and method to function in a much quieter fashion as compared to other prostheses on the market today.

As another potential benefit, the sensored brushless motors of the system and method may enable high torque at slow speeds. This benefit enables a prosthetic hand to grip objects (e.g. hammer, glass of water) without slipping.

As another potential benefit, the sensored brushless motors of the system and method may additionally enable fast motion of the prosthetic assembly. Specifically, the entire prosthetic hand may go from a completely open configuration to a closed figuration in <0.2 s. This can be two to three times faster than common competitor speeds of around 0.5 s.

As another potential benefit, sensored brushless motors typically require significantly less power for motor actuation for motors of similar capacity. Utilizing sensored brushless motors enables battery operation of a prosthetic hand to significantly decrease. Considering the size of a prosthetic hand as a significant limiting factor in the size of an implemented battery, efficient battery usage may significantly increase the time activity span of the prosthetic hand prior to requiring recharging.

Additionally, the wattage needed for sensored brushless motors may also be less than for a similar brushed motor. As an additional potential benefit of battery efficiency, the system and method may enable simultaneous actuation of multiple motors; wherein typically the limited size battery (due to hand size) limits the number of motors with sufficient power that may be active simultaneously as compared to a brushed motor of similar power.

Both power and precision of the sensored brushless motors may have the added benefit of enabling high-level coordinated actuation. High-level coordination may include complex manipulation of objects, such as tying a knot in a rope (e.g. gripping and releasing quickly enough such that the knot in the rope does not slide) or catching a ball (coordinated fast gripping with all fingers).

Another added potential benefit may be the longevity of brushless motors. The most common cause of failure of brushed motors is the degradation of the mechanical brushes; therefore, brushless motors typically have greater longevity than brushed motors. The system and method may give the benefit of a prosthesis with an extended lifespan, such that the prosthetic hand may require fewer repairs or longer use prior to requiring the device to be replaced.

The sensored brushless motors of the system and method may include both non-backdrivable and backdrivable gearboxes enabling specialized utilization of the prosthetic assembly. A non-backdrivable gearbox for fingers of a prosthetic hand may enable the prosthetic hand to grab and carry higher loads than a finger using a backdrivable gearbox. A backdrivable gearbox for the thumb may give the benefit of a manually adjustable grip of the hand on an object. A backdrivable gearbox for any finger may additionally enable utilizing the sensored brushless motor to measure external forces exerted on the finger.

Another potential benefit of the non-backdrivable gearbox may be improved energy efficiency and extended battery life. Once a prosthetic hand grips an object, no additional energy needs to be exerted by the motor to continue gripping the object.

The system and method employ miniaturized motor components that give the added benefit of a lighter prosthetic assembly. A lighter prosthetic assembly would be both less exhausting and more comfortable for a user and allow for longer concurrent use providing for a better user experience.

The system and method can be used with any suitable type of prosthesis. Herein, the system and method are primarily described as it applies to a prosthetic hand but the system and method is not limited to hand prostheses and can be used for other types of prostheses, exoskeletons, or other suitable systems. A prosthesis of the system and method may be used with any person/patient requiring a replacement limb, particularly a replacement hand. The system and method may be also implemented with an animal to provide a replacement limb. The system and method may additionally provide limb functionality a-la carte. That is, provide an additional limb to a person (e.g. third hand), or just provide a functioning limb for demonstration or study purposes as desired.

2. System

Figure 2:
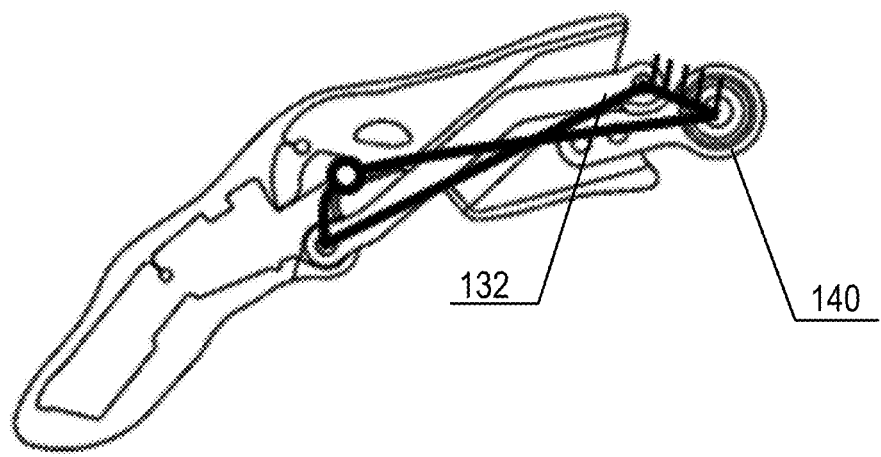
FIG. 2 is a schematic representation of an actuating system of a preferred embodiment.
Figure 3:
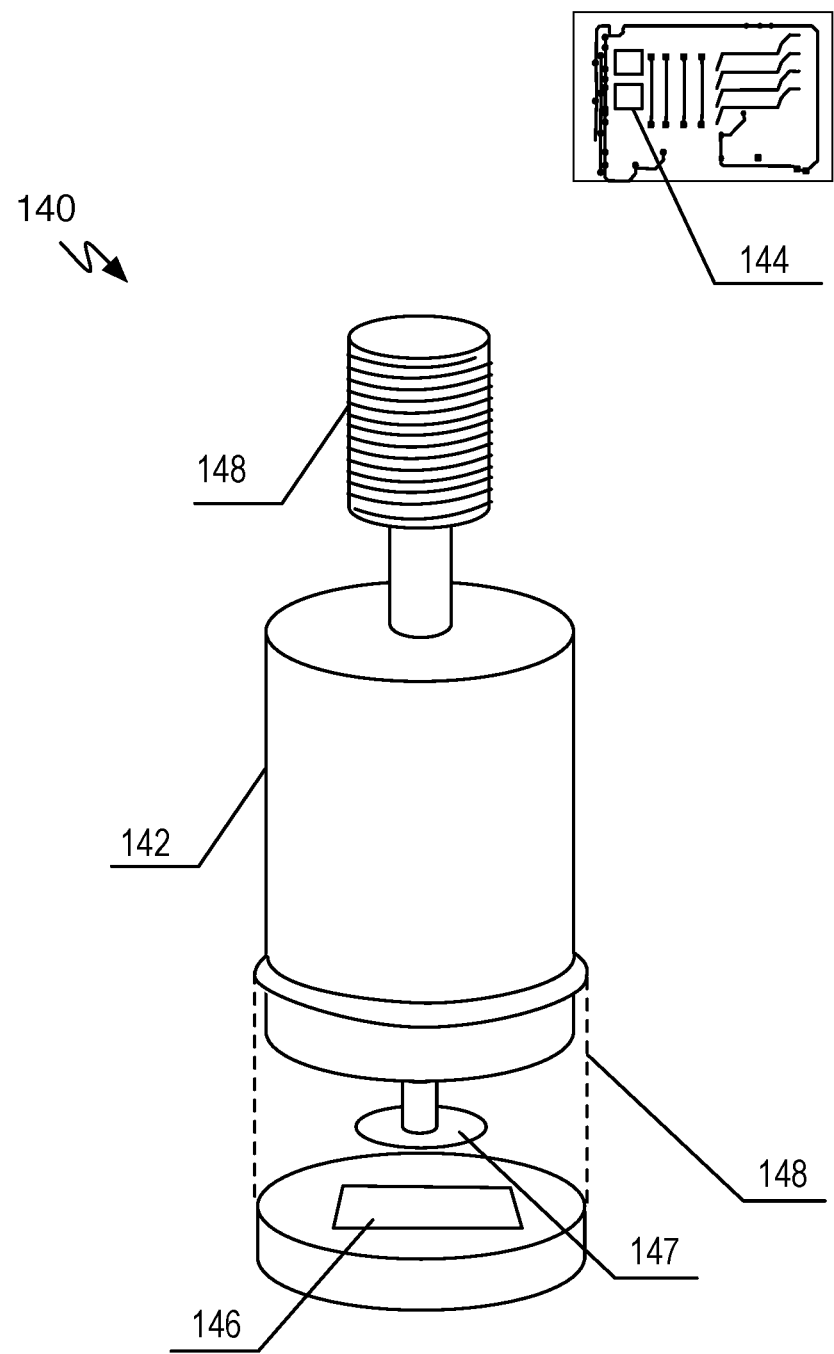
FIG. 3 is a schematic representation of a sensored brushless motor of a preferred embodiment.

As shown in FIG. 1, a system for a prosthetic assembly that includes a first prosthetic component 110, a set of second prosthetic components 120, and a set of actuating systems 130, wherein one actuating system connects a pair of distinct prosthetic components, enabling actuation of one prosthetic component with respect to the other. In general, the first prosthetic component no serves as a base component (e.g., a hand base/palm component) to which a plurality of second prosthetic components (e.g., finger components) are coupled through one or more actuating systems 130. As shown in FIG. 2, each actuating system from the set of actuating systems 130 includes a linkage 132 and a sensored brushless motor 140. The sensored brushless motor is preferably a motor system that includes a brushless motor 142, a field oriented control (FOC) control system 144, a rotary encoder 146, and a gearbox 148, as shown in FIG. 3.

Figure 4:
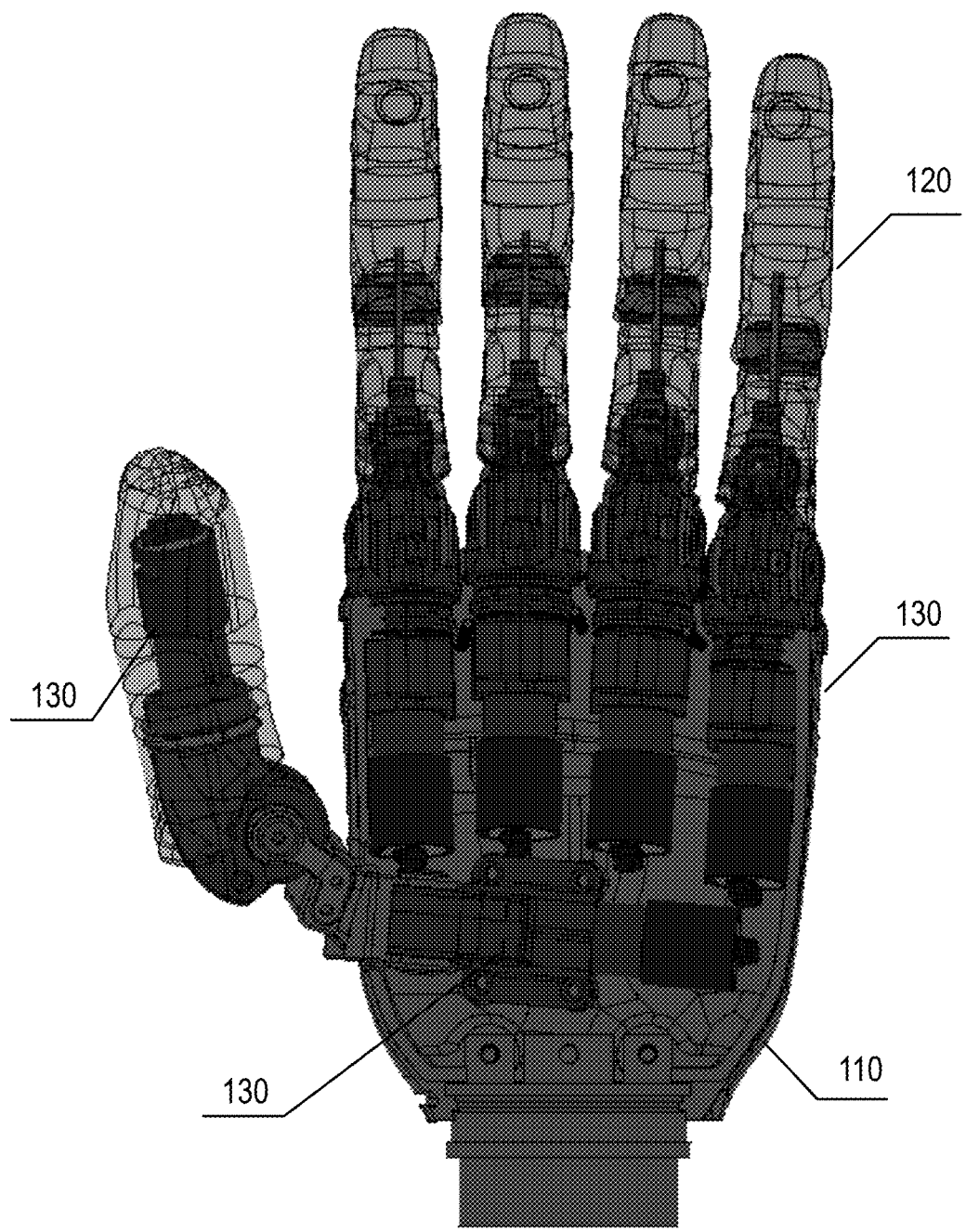
FIG. 4 is a model representation of a prosthetic hand with the embedded actuating system.
Figure 5:
FIG. 5 is a model representation of a prosthetic hand.

In preferred variations, the prosthetic assembly comprises a prosthetic hand, wherein the first prosthetic component 110 is a prosthetic hand base and the set of second prosthetic components 120 comprise a set of prosthetic fingers, wherein each finger is connected to the hand base by an actuating system 130 such that each finger may independently actuate with respect to the hand base. In some preferred variations, the system includes additional finger and/or joint components. FIG. 4 shows an internally exposed model representation of the prosthetic hand wherein the set of actuating systems are shown to each couple to at least one of the prosthetic fingers. As also shown in the prosthetic thumb of FIG. 4, multiple actuating systems 130 may cooperatively couple to a single prosthetic finger to provide multiple degrees of freedom. As shown in FIG. 5, the prosthetic assembly can preferably be assembled so as to enable a prosthetic hand with appropriate size and dimensions. In some alternative variations, one actuating system may be used in the actuation of multiple prosthetic components. For example, one actuating system 130 may couple to two prosthetic fingers for actuating both prosthetic fingers together.

Preferably the system includes a thumb joint, and a thumb prosthetic finger, wherein a first actuating system connects the thumb prosthetic finger to the thumb joint, and the another actuating system connects the thumb joint to the hand base. As shown in FIG. 4, the actuating systems may be inverted in orientation so that the first actuating system is housed in the distal portion of the thumb prosthetic finger. The system may further include other prosthetic components as desired (e.g. proximal phalanges, intermediate phalanges, distal phalanges, arm, shoulder, etc.).

In one system of a preferred implementation, the prosthetic assembly includes a prosthetic hand and a set of actuating systems. The prosthetic hand comprises a hand base and a set of prosthetic fingers. The set of prosthetic assembly comprise four prosthetic fingers, a thumb prosthetic finger, and a thumb joint, wherein each of the four fingers and the thumb joint are connected to the hand base by an actuating system, and the thumb prosthetic finger is connected to the thumb joint by another actuating system.

Prosthetic components of the prosthetic assembly may be constructed of any desired material. In preferred variations, material type is preferably chosen between a balance of several factors that may include: weight, durability, and prosthetic function. Examples of material type for prostheses include: plastics, such as polyethylene, polypropylene, acrylics, and polyurethane; wood; rubber; lightweight metals, such as titanium and aluminum; and composites, such as carbon fiber. In the same manner, prosthetic components may be hollow (e.g. to include motors) or solid constructions (e.g. for durability) as desired. Material type, composition, and shape of the prosthetic component preferably depend on the specific component and desired functionality. For example, a prosthetic hand built for aesthetic "functionality" may be primarily constructed of silicone and built to resemble, as closely as possible a human hand; while a prosthetic hand built for an advanced "grabbing motion" may have little resemblance to a human hand. In preferred variations, the prosthetic components resemble their human analogs and are built for durable functionality, although any other preferred embodiment of prosthetic components may be implemented with the system.

In preferred variations for a durable prosthetic assembly, prosthetic components may have a carbon-fiber shell that encases internal structures. The carbon-fiber shell is preferably composed of prepreg carbon-fiber molded to the form of substructures. The carbon-fiber shell may additionally be finished with a coating, e.g. 2 k urethane clear coat, but may be coated in any suitable coating. Prepreg carbon-fiber is a carbon-fiber weave pre-impregnated with resin epoxy or other suitable type of adhesive. Alternatively, a non-prepreg carbon-fiber material can be impregnated or treated with a resin epoxy or otherwise adhered and integrated onto an internal substructure.

It should be noted that unless explicitly stated otherwise, distinction between the first prosthetic components 110 and second prosthetic components 120 is purely functional in nature. That is, a second prosthetic component 120 of a preferred embodiment is considered the actuating component with respect to a "fixed" first prosthetic component 110 (or respect to itself for a deformation). In variations where there are multiple actuating components in a chain (e.g. prosthetic arm or a finger with multiple actuated joints), a prosthetic component may be referred to as a first prosthetic component 110 with respect to one prosthetic component and referred to as a second prosthetic component 120 with respect to another prosthetic component. For example, for a prosthetic arm, a prosthetic hand may be first prosthetic component 110 with respect to actuating prosthetic fingers; but may be referred to as a second prosthetic component 120 with respect to a prosthetic forearm. In systems of a preferred embodiment, the system includes at least one actuating element between a first prosthetic component 110 and a second prosthetic component 120.

The prosthetic components that are referred to herein as discrete components may comprise multiple sub-components and sub-assemblies. For example, a prosthetic hand base may comprise multiple subcomponents attached together. Furthermore, the distinct prosthetic components may be integrally linked such that they are directly coupled through one or more physical structure(s). For example, a hand base and a finger may be 3D printed together. The hand base and the finger preferably are still coupled through an actuating system 130 enabling actuation of the finger relative to the "connected" hand base.

The first prosthetic component 110 of a preferred embodiment functions as a base, "fixed", component to enable relative motion of the set of second prosthetic components 120. The first prosthetic component 110 may be connected to one or multiple second prosthetic components (e.g. multiple components from the set of second prosthetic components 120, other prosthetic and non-prosthetic components). In preferred variations, the first prosthetic component 110 is connected to the second prosthetic component by an actuating system 130.

The first prosthetic component 110 may be attached directly to a patient/user, wherein the first prosthetic component may have any indentation, socket, extension, and/or any other required shape such that the prosthetic assembly may be attached and/or worn by the user. Alternatively, the first prosthetic component 110 may connect to other prosthetic assembly components. For example, a prosthetic hand first prosthetic component 110 may connect to a prosthetic forearm.

The set of second prosthetic components 120 of a preferred embodiment function as actuating components. When applied to an actuating prosthetic hand, a second prosthetic component 120 is preferably a prosthetic finger. The prosthetic finger may be or be integrated with a linkage 132. For example, the prosthetic finger may actuate in as part of a four-bar linkage coupled to an actuating system 130 such as shown in FIG. 2. Actuation of second prosthetic components may be relative to the first prosthetic component no (e.g., bending of a finger relative to the hand) or may be a deformation of the second prosthetic component (e.g., folding the tip of a finger).

The actuating system 130 of a preferred embodiment, functions to provide a mechanism and driving force for actuation of a prosthetic component. The actuating system 130 and/or subcomponents of the actuating system may have additional functional roles (e.g. structural durability). The actuating system 130 may connect the first prosthetic component 110 to the second prosthetic component 120 and provide a mechanism of actuation of the second prosthetic component relative to the first prosthetic component. The actuating system 130 preferably comprises a linkage and a sensored brushless motor. Dependent on the desired functionality of an actuating system 130, actuating systems from the set of actuating systems may differ. For example, linkage components may differ to enable sliding motion, motor gear components may differ to provide preferred unidirectional or bidirectional motion.

Figure 6:
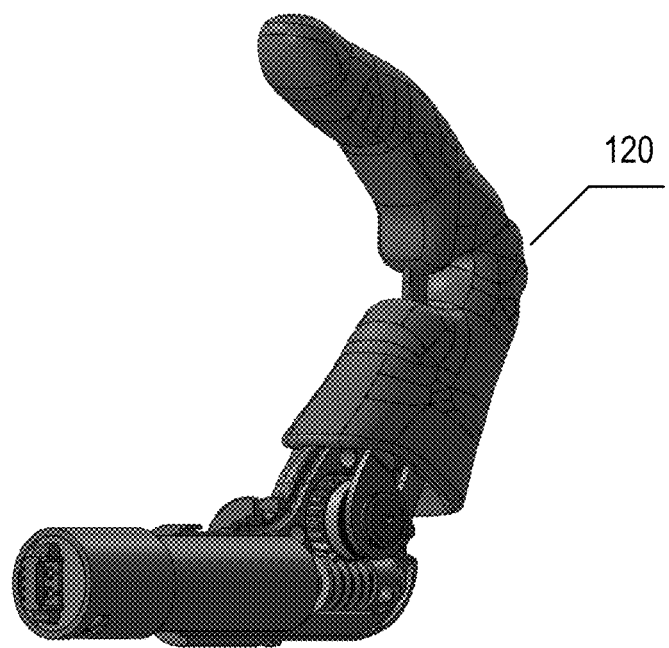
FIG. 6 is a model representation of a prosthetic finger component of the prosthetic hand.

In many variations, the actuating system 130 is a flexor system providing muscle flexor type actuation (i.e. motion similar to flexing/contraction of muscles). It should be noted that the flexor system, as used herein, refers to muscle flexor type actuation in the broadest sense. That is, actuation preferably occurs through motor driven contraction of appendage linkages and/or prosthetic components; and/or actuation through motor driven contraction between appendage linkages and/or prosthetic components. As desired, the actuation system may provide non-flexor type actuation. For example, in some variations, actuation may additionally or alternatively occur through component extension, component rotation, rigid translation of a component, rigid rotation of a component, and/or any other method of actuation. FIG. 2 shows an example of a flexor system within a prosthetic finger, wherein a brushless motor drives contraction of the prosthetic finger by contracting the appendage linkage embedded within the prosthetic finger. For the prosthetic hand example, the prosthetic assembly preferably includes at least five flexor systems, wherein each flexor system connects the hand base to a corresponding prosthetic finger. Additional or fewer flexor systems and/or prosthetic fingers may be implemented as desired. FIG. 6 shows a model representation of a prosthetic finger with an actuating flexor system.

Figure 7:
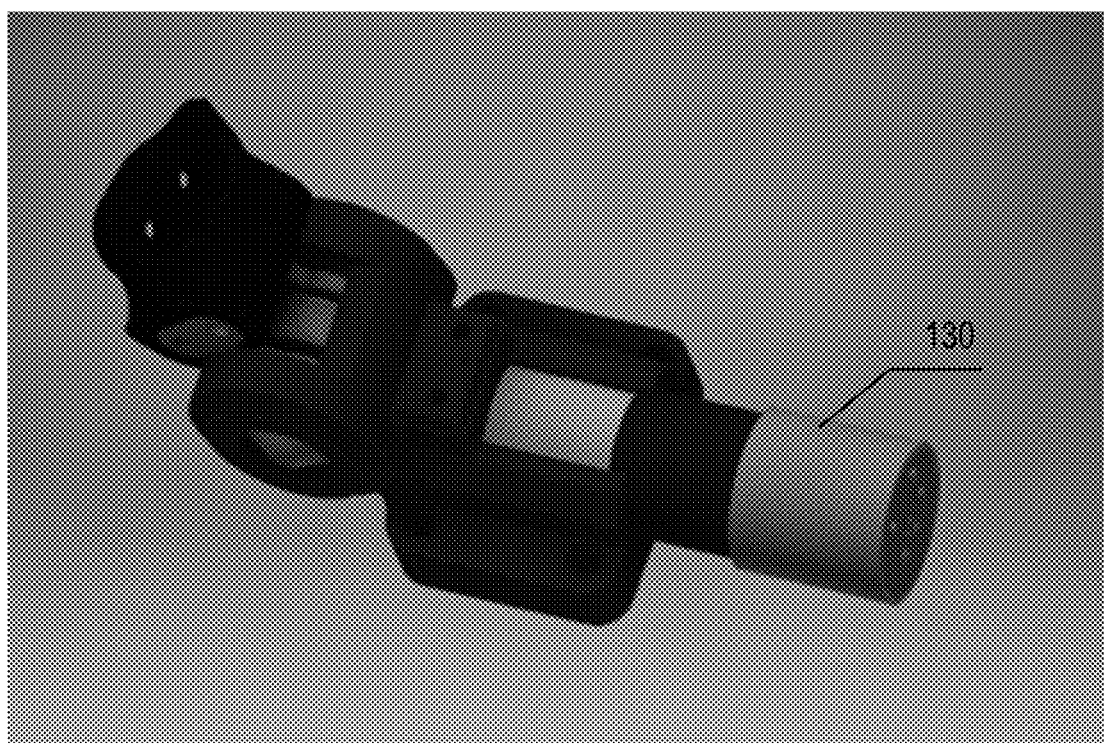
FIG. 7 is a model representation of the actuating system of a prosthetic thumb.

The prosthetic hand preferably contains an additional actuating system 130 in the thumb of the prosthetic hand. In these preferred variations, the thumb has two actuating systems 130, wherein one actuating system 130 enables thumb opposition internally and externally; and a second actuating system 130 that enables thumb flexion and extension. Bending of the thumb functions to enable grasping with the prosthetic hand. Preferably, the gear components of the two thumb actuating systems differ (e.g. the motor of one actuating system may have a standard worm-gear, wherein the other actuating system may have a motor implemented with a worm-gear with a slanted thread. FIG. 7 shows the flexor actuating component of the thumb.

The linkage 132 is preferably a component of the actuating system 130. The linkage functions as a support and/or joint structure for one or more prosthetic components. Additionally, the linkage 132 preferably provides a mechanism to actuate the prosthetic component. As desired, the linkage 132 may connect the two prosthetic components in a fashion such that they are rigidly connected or have some desired degree(s) of motion. For the prosthetic hand example, the linkage 132 between the hand base and the digital prosthetic fingers is preferably a 4-bar linkage, wherein one 4-bar linkage would connect the prosthetic hand to a prosthetic finger as shown in the side view of a prosthetic finger in FIG. 2. Additional 4-bar linkages may be implemented to connect and enable motion of other prosthetic components. Based on functionality and other requirements, different appendage linkages may be used as desired.

As a support structure, the linkage 132 may be internally embedded within the prosthetic components, outside of the prosthetic components, or some combination of the two. The linkage 132 preferably provides resistance to deformations (e.g. contortions, extensions, contractions, compressions). The structure and composition of the linkage 132 preferably incorporate different magnitude resistance forces for different deformations, wherein "desired" deformations may be considered compliant and have less resistance than "undesired" deformations.

The linkage 132 may additionally function as a joint and/or connector between prosthetic components. As desired, the linkage 132 may connect the two prosthetic components in a fashion such that they are rigidly connected or have some desired degree(s) of motion. For example, a linkage 132 may connect the prosthetic hand to a prosthetic finger with preferably at least one degree of freedom controlled by an actuating system 130.

The 4-bar linkage is preferably a component of the linkage. The 4-bar linkage functions as an appendage linkage that connects the prosthetic finger to the prosthetic hand that includes joints for finger actuation. The 4-bar linkage may be a commercially available 4-bar linkage, which comprises four bars (i.e. links) connected by four joints.

Alternatively, in preferable variations, the linkage 132 is a compliant 4-bar linkage. The compliant 4-bar linkage may function as a "less rigid" linkage that is preferably more resilient to impact from multiple angles, as compared to rigid linkages (e.g. rigid, commercially available 4-bar linkages). The compliant 4-bar linkage system may depend on higher levels of torque during actuation. As an alternative to a standard 4-bar linkage, that comprises four links and four joints, the compliant 4-bar linkage preferably comprises: a compliant monolithic bone, that serves as the coupler and input links; a follower link; and a ground link. Additionally, the compliant 4-bar linkage replaces a revolving joint, a proximal interphalangeal (PIP) joint with a compliant joint. That is, compliance is added to the linkage through the compliant monolithic bone and a follower link comprising at least one, but preferably three, layers of pre-stressed spring steel. This mechanism of the compliant 4-bar linkage behaves like a conventional 4-bar linkage but adds lateral compliance and eliminates a revolute pin joint. Elimination of the revolute pin joint may significantly improve the impact resistance of the compliant 4-bar linkage, while adding greater resistance to finger actuation. Additionally, the monolithic compliant bone and fewer components also increase the impact resistance and reduce the friction of the compliant 4-bar linkage while adding lateral compliance.

The linkage 132 may function as a neutral resistance linking joint. That is, the linkage 132 provides relatively equal resistance for any type of actuation of the second prosthetic component 120 with respect to the first prosthetic component 110. Alternatively, the linkage 132 may define a stable "rest position," wherein the linkage 132 provides greater resistance away from the rest position and exerts a restoring force to the rest position. Both types of appendage linkages may be employed as desired. In the prosthetic hand, the appendage linkage for each finger preferably has a closed-hand rest position, such that the hand will return to a closed-hand configuration if no other forces are exerted on the hand. For different functionalities, an appendage linkage with a different rest position may be employed (e.g. an open-hand rest position). In the preferred variation, each individual finger can hold up to 17.23 kg and return to the rest position, and the grasp of the entire hand can hold up to 23.06 kg and return to the rest position.

The sensored brushless motor 140 is preferably a component of the actuating system 130. The sensored brushless motor 140 functions to drive actuation of moving prosthetic components. The sensored brushless motor 140 preferably includes a control system, an encoder, and a gearbox. In preferred variations, the sensored brushless motor 140 comprises a field oriented control (FOC) control system 142, a rotary encoder 144, and a gearbox 146. The sensored brushless motor preferably provides greater torque at greater speeds for short actuations, as compared to brushed motors. In preferred variations, that include the compliant 4-bar linkage, the sensored brushless motor 140 provides the necessary additional torque to actuate compliant joints.

In preferred variations, the sensored brushless motor 140 functions as part of the flexor system, wherein the sensored brushless motor provides drive for contraction actuation of prosthetic components. Preferably, the sensored brushless motor 140 can generate sufficient torque to overcome the restoring force of the linkage 132 to drive the contraction actuation. In some preferred implementations, disengagement of the sensored brushless motor 140 allows the restoring force to return the prosthetic component to the rest position. In some alternate preferred implementations, the sensored brushless motor 140 drives all actuations (e.g., both contraction and extension as part of a flexor actuating system 130).

The sensored brushless motor 140 preferably has greater torque, as compared to brushed motors of similar size. The sensored brushless motor 140 is preferably sufficiently small such that a plurality of brushless motors may fit inside, or between, the first prosthetic component 110 and second prosthetic components 120. For the preferred prosthetic hand example, at least five sensored brushless motors 140 fit within the prosthetic hand base. More preferably, the prosthetic hand may contain six sensored brushless motors 140; two for the thumb and one each for the four other prosthetic fingers. In preferred implementations, the sensored brushless motors 140 for the prosthetic hand may be less than 15 mm in diameter (e.g., 12 mm) and 20 MM in length, though smaller or larger motors may alternatively be used.

The brushless motor 142 is preferably a component of the sensored brushless motor 140. The brushless motor 142 functions as the motor that generates torque. Preferably, the brushless motor 142 provides a higher power-to-weight ratio, higher speeds, and better durability, as compared to a similar sized brushed motor. The brushless motor may be an inrunner motor (i.e. where the rotor is inside the stator of the motor) or an outrunner motor. In preferred variations for a prosthetic hand, the brushless motors 142 are positioned in the hand base. For this variation, the system preferably includes six brushless motors 142, one for the actuation of each hand digit, and two motors for the actuation of the thumb prosthetic finger.

The sensored brushless motor 140 preferably includes a field-oriented control (FOC) control system 144, herein the combination of the brushless motor and FOC control system are referred to as an FOC brushless motor. Alternative control systems (e.g. trapezoidal controlled brushless motors) may be implemented. In one implementation, a control system preferably enables satisfying design criteria such as motor size (e.g. 12 mm diameter×20 mm length), motor weight (e.g. 10 g), motor sound generation (e.g. <73 dB at 1 m), motor stall torque (e.g. >9.00 mN*m), torque at maximum power transfer point (e.g. >4.53 mN*m). The control system 144 is preferably powered by a DC power source (e.g. battery). In some preferred variations, the control system includes circuitry to convert the DC source to an AC for the motor.

FOC is a variable-frequency drive control method in which stator currents of a three-phase AC electric motor are identified as two orthogonal components that can be visualized with a vector. The two orthogonal components define the magnetic flux and the torque. The FOC control system 144 calculates motor flux and torque current components using a combination of phase current measurements from the driven stator windings and the rotor position measured by the encoder, and adjusts the output phase voltage to track a given reference motor torque. The FOC electronics may enable the brushless motor to function smoothly over the full speed range of the motor and generate full torque at zero speed, thereby enabling continuous torque control. While market FOC brushless motors are too large to fit within a prosthetic hand, the system preferably includes miniaturized FOC brushless motors with satisfying specifications listed above that do fit within the prosthetic hand.

Figure 8:
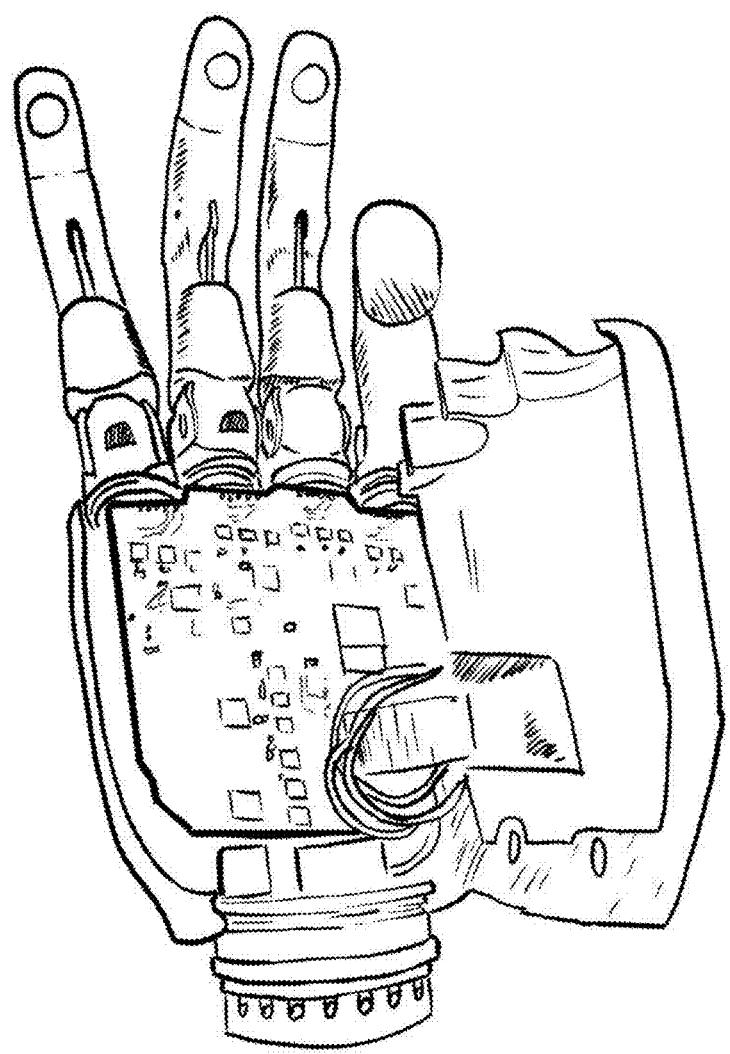
FIG. 8 is a picture representation of the FOC circuit board within the hand base.

In preferred variations, for a prosthetic hand with six actuating systems (i.e. six FOC controllers), the FOC controllers are positioned on a printed circuit board (PCB) that is housed within the hand base. FIG. 8 shows one implementation of the FOC on a PCB in the hand base of a prosthetic hand.

The sensored brushless motor 140 preferably includes a rotary encoder 146. The rotary encoder 146 functions to measure and report the absolute angular position of the rotor of the brushless motor 142 to the FOC control system 144. The rotary encoder 146 is preferably an absolute rotary encoder, but may alternatively be an incremental rotary encoder. In preferred variations, the absolute rotary encoder is a Tunneling Magnetoresistance (TMR) sensor. The TMR sensor enables highly dynamic torque control of the FOC brushless motor. The FOC brushless motor may alternatively include another encoder as long as the encoder is sufficiently small, precise, and fast (e.g. continuous Hall sensor).

The TMR sensor is preferably an external encoder. The TMR sensor may include a 4-pin connector. In preferred variations for a prosthetic hand, each TMR sensor is axially aligned with and offset from a backshaft side of the brushless motor 142. A magnet 147 is preferably physically coupled to a backshaft of the brushless motor. The magnet 147 is preferably a disc magnet that is coaxially coupled to the backshaft as shown in FIG. 3. Preferably, the TMR sensor is fixed relative to the back shaft of the brushless motor such that there is an air gap between the motor magnet 147 and the TMR sensor. The air gap is preferably between 0.05 mm to 2 mm. In some preferred variations, the air gap is 0.4 mm. A motor sensor housing 148 preferably couples to the back portion of the motor brushless motor 142 and holds a TMR sensor in position relative to the magnet 147. The TMR sensor can preferably be rotated for calibration to the brushless motor 142. In preferred variations, the positioning of the encoder may enable calibration of the FOC brushless motor.

For the rotary encoder 146 to function properly, i.e., correctly measure and report the absolute angular position of the rotor, the rotary encoder must be calibrated such that the actual rotor position of the brushless motor matches the detected rotor position of the rotary encoder within some desired degree of accuracy. Calibration may occur through a software offset wherein the detected rotor position value is offset by a sufficient value such that it matches with the actual rotor position. Alternatively, calibration may occur through a "hardware" offset wherein angular positioning of the rotary encoder 146 or the motor is adjusted until the two values match. In some preferred variation, the calibration occurs through a hardware offset.

For the preferred variation of a prosthetic hand with multiple fingers, calibration for each sensored brushless motor 140 is carried out identically to physically calibrate the position of the encoder for universal identical calibration. That is, each brushless motor is identically calibrated to its respective rotary encoder to have the same mechanical offset, such that the calibration for all prosthetic fingers is synchronized. The universal calibration can make the sensored brushless motors 140 interchangeable during assembly and/or maintenance. Synchronized calibration of the prosthetic fingers may enable simpler prosthetic finger replacement, such that any prosthetic finger, from the set of prosthetic fingers, is "hot-swappable", such that it may be removed and replaced with a new prosthetic finger without any additional adjustments or calibrations.

The sensored brushless motor 140 preferably includes a gearbox 148. The gearbox 148 enables transfer of the brushless motor torque to the actuating elements of the prosthetic assembly, to drive actuation of the second prosthetic component 120. FIG. 6 shows one preferred implementation of a worm drive gearbox 148 within the prosthetic finger. The gearbox 148 of the sensored brushless motor 140 may be either a non-backdrivable gearbox or backdrivable, depending on the implementation. In some variations, the sensored brushless motors 140 of each actuating system 130 that connects each prosthetic finger to the prosthetic hand include a non-backdrivable worm drive gearbox 148. Alternatively, the gearbox 148 may be a helical gearbox, a coaxial helical gearbox, a bevel helical gearbox, a skew bevel helical gearbox, a planetary gearbox, or any other gearbox with desired functionality. The worm drive gearbox 148 may enable high torque, low speed actuation and high torque, small displacement actuation. The worm drive gearbox 148 may additionally enable better miniaturization of the sensored brushless motor 140.

In some preferred variations, the gearbox 148 is non-backdrivable. While the exerted torque of the sensored brushless motor 140 must overcome any resistance (e.g. due to an object the prosthetic finger wishes to grip), once the prosthetic finger has flexed and gripped an object, the non-backdrivable worm drive gearbox 148 may enable maintained contraction of the prosthetic finger without continued force exertion of the motor. That is, the non-backdrivable worm drive gearbox 148 may generally hold the position of the prosthetic finger with no energy going to the motor, thereby creating a stable rest position until disengagement of the gearbox 148.

The sensored brushless motor 140 may alternatively include a backdrivable gearbox 148. The backdrivable gearbox 148 may enable backdrivable actuation of a prosthetic component. In addition to providing actuation, a backdrivable gearbox 148 may enable the sensored brushless motor to be used as a force or contact sensor. The force over the area of the prosthetic component may be determined by measuring the torque exerted by the sensored brushless motor 140 to a matching force exerted on the connected actuating prosthetic component. In a second variation, the sensored brushless motor 140 of the thumb may include a backdrivable gearbox to enable fine-tuning of gripping an object. In another variation, a finger may include a backdrivable gearbox 148 to enable the finger to be force sensitive.

Figure 9:
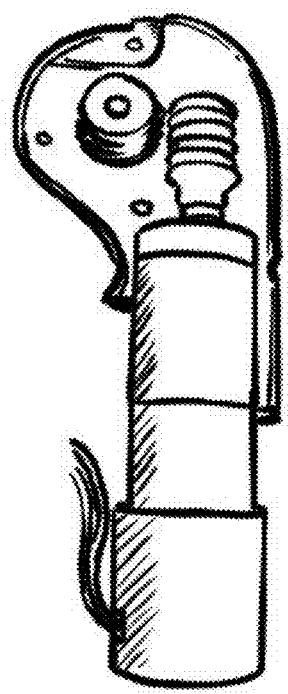
FIG. 9 is a picture representation of the sensored brushless motor encased in a housing.

In preferred variations, the sensored brushless motor 140 may additionally include a sensored brushless motor housing (i.e. SBM housing). FIG. 9 shows a picture of the sensored brushless motor in a half open SBM housing. The SBM housing may function to enable easy accessibility to the brushless motor 142. Easy accessibility may be helpful in maintenance and calibration of the brushless motors 142. In this preferred implementation, the SBM housing is a roughly cylindrical structure that encases the entire sensored brushless motor, wherein the encoder is embedded at one end, and the gear-box (e.g. worm gear) is exposed within the housing near the other end of the SBM housing. In this exposed area, the gear-box preferably connects to the drive shaft of the linkage mechanism connected to the prosthetic finger.

In preferred variations for a prosthetic hand, the system may further include a hand or arm socket (referred to as arm socket). The arm socket element preferably interfaces between the residual limb of the user and the prosthetic hand. In some variations, the arm socket may have an additional rotational degree of freedom with an actuator system 130 in a wrist-region where the palm body interfaces with the arm socket element. In other variations, a multi-degree of freedom and multiple actuator systems 130 may be implemented to allow the prosthetic hand to be actuated in multiple dimensions relative to the arm socket element.

The arm socket element is preferably a shell structure designed to fit over the user's residual limb. Accordingly, the arm socket element may include a defined recessed cavity. The arm socket element is preferably substantially rigid. In some variations, the arm socket element may additionally include an external carbon-fiber shell. Padding and other elements can be integrated into the defined recessed cavity to increase comfort for the user.

The system may additionally include a control system. The control system may function to allow user control of the prosthetic assembly. For the prosthetic hand variation, the control system may be preferably a user control input. In one variation, the control input may be located in the arm socket. The control inputs may include electromyographic sensors that are used to sense user input. Preferably, the control input is controllably coupled to the set of sensored brushless motors, configured to perform simultaneous and independent actuation of the sensored brushless motors. A processor or digital circuit preferably translates input sensed by the electromyographic sensors into control inputs for the prosthetic hand, more preferably for the set of actuating systems 130.

The control system may include electronics, circuitry, and/or other computational system elements used in control of the actuated hand as well as other electronic elements such as a battery and communication modules. Some and/or all of these elements may be located in the arm socket, in/on the prosthetic hand, or in some combination of the two. Alternatively, such elements may be housed in any suitable portion of the system. In some variations, a portion of such elements may even be communicatively coupled through a wired or wireless connection.

For the preferred prosthetic hand example, different variations of actuating systems 130 and different subcomponents (e.g. additional motors) may be added or removed for desired functionalities. For example, the last three prosthetic fingers of the prosthetic hand may implement non-backdrivable worm drive gearboxes 148 to optimize gripping/holding and carrying loads, while the pointer finger prosthetic finger incorporates a backdrivable gearbox 148 to function as a sensing finger, and the thumb prosthetic finger incorporates both a rotational actuation and backdrivable gearbox to optimize fine touch gripping.

Figure 10:
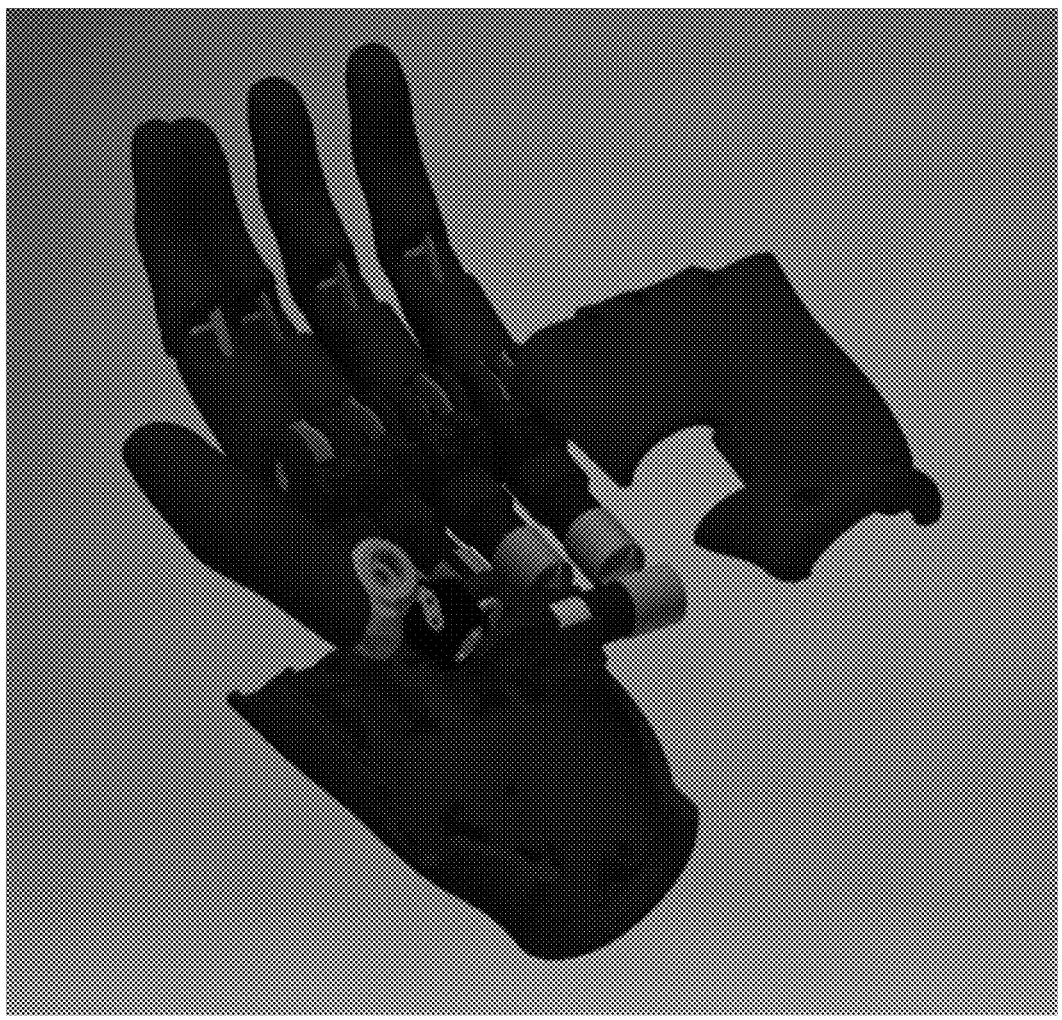
FIG. 10 is a model representation of a blown out prosthetic hand.

As described herein, a preferred example of the prosthetic assembly is a prosthetic hand. FIG. 10 shows a model representation of the prosthetic hand, wherein the hand base is blown out to show the actuating system 130 connected to the prosthetic fingers. The prosthetic hand is preferably an average size female hand, but may be of any size larger or smaller size (e.g., the prosthetic hand may be a child size hand or an adult male hand). The prosthetic hand may comprise a first prosthetic component no prosthetic hand base, and a set of second prosthetic components 120 comprising five prosthetic fingers; four digit prosthetic fingers and one thumb prosthetic finger.

Each prosthetic finger is connected to the prosthetic hand by an actuating system 130, wherein the actuating system comprises a 4-bar linkage and a sensored brushless motor 140. The 4-bar linkage is preferably a compliant 4-bar linkage, wherein the majority of the monolithic compliant bone for each compliant 4-bar linkage is embedded within each prosthetic finger, similar to a skeleton. The actuating joint of the compliant 4-bar linkage is at the base of each prosthetic finger and connects to a sensored brushless motor 140 embedded within the prosthetic hand; one sensored brushless motor per finger digit and two sensored brushless motors for the thumb.

The sensored brushless motor 140 is preferably a brushless motor 142, an FOC control system 144, a TMR sensor rotary encoder 146, and gearbox 148. The brushless motor 142 is preferably incorporated in the hand base within proximity of the prosthetic finger powered by the brushless motor. The body of the brushless motor 142 is preferably encased in a SBM housing positioned in the hand base, with a disk magnet situated on the back shaft of the brushless motor. The TMR sensor is preferably axially calibrated to the brushless motor along the back shaft and positioned, within the SBM housing, such that the TMR sensor is proximal to the disk magnet with a defined gap between the TMR sensor and the disk magnet.

Each sensored brushless motor 140 preferably has a bidirectional worm gearbox 148 that enables conversion of the motor torque into finger bending actuation. The bidirectional worm gearbox 148 may either be non-backdrivable, preventing movement of the drive gear from external loads, or backdrivable, allowing external forces to spin the drive motor and drive gear.

The non-backdrivable worm gearbox 148 optimizes gripping and holding objects, but dependent on desired finger functionality, a backdrivable gearbox may be employed for pressure sensitive functionality.

The thumb prosthetic finger preferably includes two thumb components and an additional actuating system 130, wherein one sensored brushless motor 140 functions similarly to the actuating system of the other prosthetic digits, as a flexor system. A first thumb component couples to the hand base on one end and a second thumb component on the opposite end. Additionally, the thumb preferably includes an additional sensored brushless motor 130. This additional motor enables rotational motion of the thumb. This sensored brushless motor preferably includes a worm drive gearbox, wherein gearbox grooves are slanted and not orthogonal to the long axis of the gearbox.

3. Method

Figure 11:
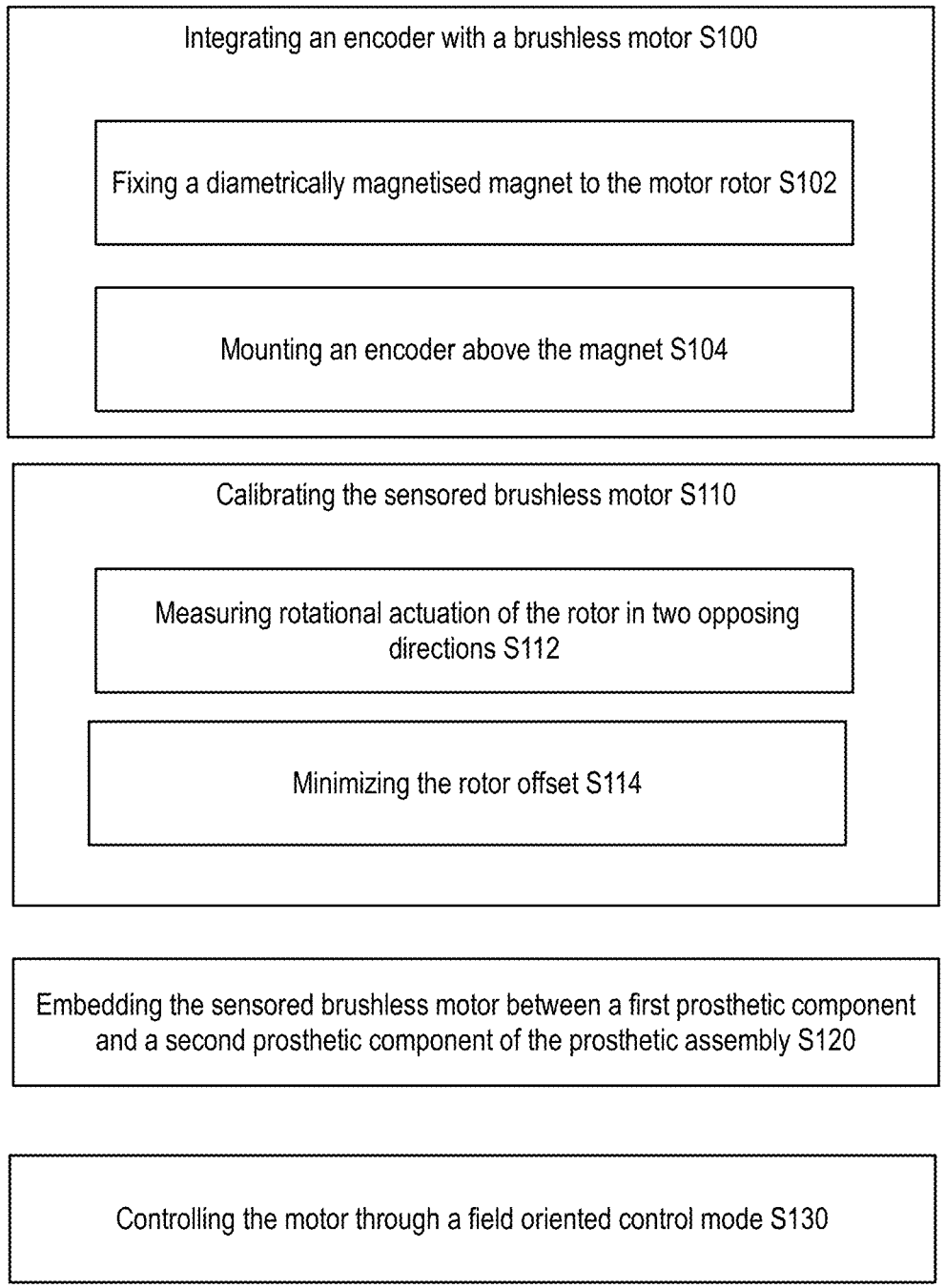
FIG. 11 is a flowchart representation of a method of a preferred embodiment.

As shown in FIG. 11, a method for implementing a sensored brushless motor system with a prosthetic assembly includes: integrating an encoder with a brushless motor S100; calibrating the sensored brushless motor S110; embedding the sensored brushless motor between a first prosthetic component and a second prosthetic component of the prosthetic assembly S120; and controlling the motor through a field oriented control (FOC) mode S130. The method enables assembly of a miniaturized sensored brushless motor system to high torque, high precision actuation for a prosthetic assembly with limited space. In particular, the method can be applied to a prosthetic hand where multiple actuated prosthetic finger components are enabled with limited volumes. In particular, the method is used in the assembly, configuration, and implementation of the system as described above, but the method may alternatively be applied to any suitable implementation.

The method may enable implementation of small, energy efficient, highly dynamic, sensored motors. Accordingly, the method may have applications well beyond the prosthetic hand. The method may be implemented as part of any general prosthetic assembly of varying size. Examples of large prosthetic assemblies include: knee, thigh, and elbow prostheses. Particularly due to the small size of the sensored brushless motors, the method may also be implemented with smaller actuating prosthetic assemblies (e.g. toes, ankles, pharyngeal finger joints).

Block S100, which includes integrating an encoder with a brushless motor, functions to assemble components for the monitoring of the motor rotor position and speed of the motor. As is often the case with miniaturization of components that either some added cost is gained or some functionality is lost or reduced; very often both are true. For the case of an electro-magnetic brushless motor, the rotor flux angle, or the position of the rotor as compared to the driving electro-magnetic field (EMF) produced by the stator, can be a critical parameter that may impact the importance to the motor driver for the motor to spin. In applications with sensors external to the motor, the location of the rotor may be routinely monitored with the encoder. Thus, integrating an encoder with a brushless motor S100 preferably includes positioning the encoder in proximity of the brushless motor such that the encoder can detect actuation of the motor (i.e. measure the rotor flux angle of the motor). And thus, in preferred variations for a prosthetic hand, integrating an encoder with a brushless motor preferably includes: fixing a diametrically magnetized magnet to the motor rotor S102 and mounting an encoder above the magnet S104. Integrating an encoder with a brushless motor S100 may thus enable field oriented control of the motor, wherein the encoder preferably monitors and reports the rotor position thereby enabling the field oriented controller to generate the appropriate field to power the actuation of the rotor.

Integrating an encoder with a brushless motor S100 preferably includes integrating an absolute encoder (i.e., rotary encoder). The absolute encoder functions to monitor the position of the rotor (or angle transducer). Preferably, a high precision absolute encoder may be used. In preferred variations, the absolute encoder is a magnetic encoder. More preferably, the absolute encoder is a tunneling magnetoresistance (TMR) sensor. In an alternate variation, the absolute encoder is a Hall effect sensor.

Block S102, which includes fixing a diametrically magnetized magnet to the motor rotor is preferably a component of integrating an encoder with a brushless motor S100. Fixing a diametrically magnetized magnet to the motor rotor S102, functions to enable external monitoring of the rotor flux angle with a magnetic encoder. In preferred variations, the magnet is a disk, or other shape, with circular symmetry (e.g. cylindrical). The magnet is preferably fixed coaxially to the motor rotor. The magnet is preferably coupled to the backshaft of the motor rotor where the backshaft is a portion of the motor rotor extending on the backside of the motor. Fixing the magnet may comprise gluing, welding, or using any other desired method of adhesion. Fixing the magnet may alternatively include physically attaching the magnet to the motor rotor through a fixture or casing that couples the back shaft and the magnet. In preferred variations, for an actuating system of a prosthetic hand, the magnet is preferably fixed to the rotor backshaft.

Block S104, which includes mounting an encoder above the magnet, is preferably a component of integrating the encoder with the brushless motor S100. In preferred variations for a TMR sensor, mounting an encoder above the magnet S104, preferably functions to enable the sensored brushless motor functionality, wherein the encoder may monitor the position of the rotor. Mounting an encoder above the magnet S104 includes positioning the TMR sensor such that it is axially aligned with the motor and in proximity of the diametrically magnetized magnet. Preferably, the TMR sensor is positioned with a small displacement from the magnet such that there is a defined gap between the two. Mounting preferably involves fixing the TMR sensor to an encoder housing that physically couples to the motor and the TMR sensor. Preferably, block S104 does not "permanently" fix the encoder positioning with respect to the motor. In preferred variations, mounting the encoder allows axial movement between the two components to allow calibration of the sensored brushless motor. Upon calibration, the mounting may be rigidly fixed to prevent adjustments.

In some preferred variations for the prosthetic hand, S100 includes integrating the motor and the encoder within a housing (i.e. motor housing) such that they are axially aligned. Preferably either the motor or the encoder are not completely fixed in place, such that at least one may be rotated to enable adjusting the offset between the motor and the encoder. For the TMR sensor example, block S100 includes embedding the motor in the housing such that a motor back shaft with the magnet are embedded within the casing and the TMR sensor is exposed on the surface of the casing. The mounting can be an endcap that is attached to the end portion of the motor and then has the TMR sensor mounted on an end plate so that the TMR sensor and the magnet are coplanar and separated by a defined gap. The angle alignment of the TMR sensor is preferably established through calibration. As shown in the blown out hand in FIG. 10, the housing may enable easy access to the encoder such that it can be adjusted for calibration.

The encoder is fixed within the housing relative to the back portion of the motor. The encoder is preferably mounted offset from the magnet attached to the back shaft of the motor within the housing as shown in FIG. 3. Preferably, the encoder is, at least initially, not locked in place such that it may be rotated in the housing to enable adjusting the offset during calibration. Though after calibration, the encoder and/or the housing may be fixed in place to prevent further adjustment.

Block S110, which includes calibrating the sensored brushless motor, functions to optimize motor functionality. Calibrating the sensored brushless motor S110 may play a critical role for motor functionality. Calibrating the sensored brushless motor can set the angular offset with respect to the true rotor flux angle and thereby avoid issues with driver inefficiency. In preferred variations, calibrating the sensored brushless motor S110 includes: measuring rotational actuation of the rotor in two opposing directions S112, and minimizing the rotor offset S114. Blocks S112 and S114 may be implemented by driving the motor in both directions, calculating the rotor offset and adjusting the angular position of the encoder (e.g., rotating an encoder mounting), and then repeating the process. Once the rotor offset is within desired tolerances the sensored brushless motor can be considered calibrated. Calibrating the sensored brushless motor S110 may be performed independently as a distinct method, or as a step in implementing a sensored brushless motor. Motors calibrated through this fashion are universally calibrated wherein software calibration may not be needed, and the motors can be interchangeable.

Calibrating the sensored brushless motor S110 may be performed independently as a distinct method, or as a step in implementing a sensored brushless motor system. As an independent method, calibrating the sensored brushless motor S110 may be generally used to calibrate any single, or set of field controlled sensored motors. Block S110, may be performed multiple times to incrementally adjust the flux offset due to the encoder positioning with respect to the motor until a desired level of calibration is reached.

In addition to calibrating a single sensored brushless motor, block S110 enables aligning/multiple aligning multiple motors in conjunction. That is, calibrating the brushless motor S110 may be additionally performed to align the rotor positioning of multiple brushless motors.

Block S112, measuring rotational actuation of the rotor in two opposing directions, is preferably a component of calibrating the sensored brushless motor S110. Measuring the rotational actuation of the rotor S112 functions to determine the offset between motor actuation in one direction versus the opposite direction. Preferably, the motor is driven with a fixed voltage (e.g. 10 V) in each direction. The rotational actuation in each direction is measured, and the difference between the measurements is taken to determine the offset. In one preferred variation, the rotational actuation is the rotor average speed, and thus measuring the rotational displacement in each direction over a fixed amount of time comprises measuring the angular speed of the rotor during the entire actuation and determining the average speed.

Block S114, minimizing the rotor offset, is preferably a component of calibrating the sensored brushless motor S110. Minimizing the rotor offset S114 preferably functions to reduce the rotor angular offset, such that the offset is below a desired threshold. Minimizing the rotor offset S114, adjusts either the encoder "perceived" positioning of the rotor (e.g. through software), or physically adjusts the angular positioning between the encoder and the motor. In preferred variations, the physical positioning is adjusted, but alternatively a software perceived positioning, or a combination of a physical and software adjustment may be implemented. Minimizing the rotor offset S114, is preferably an incrementally implemented step, wherein block S114 may be implemented multiple times to gradually minimize the rotor offset until it is below the desired threshold.

Figure 12:
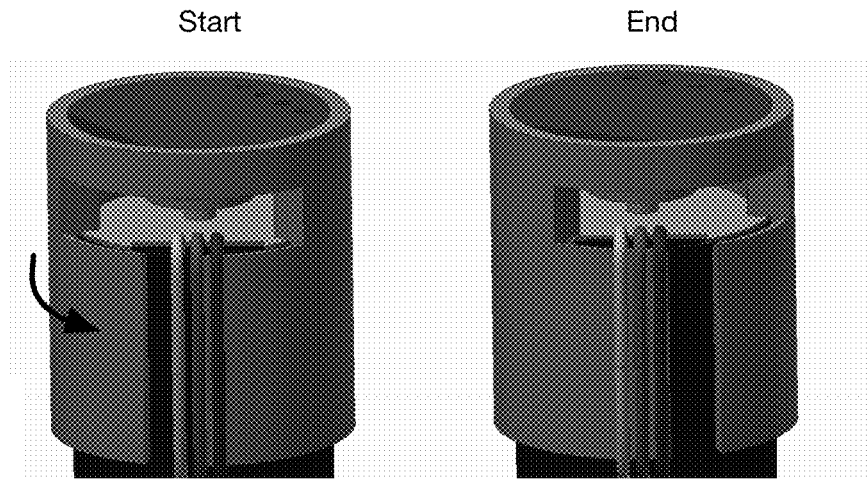
FIG. 12 is a model representation of calibrating the sensored brushless motor of a prosthetic finger of a preferred embodiment.
Figure 12:
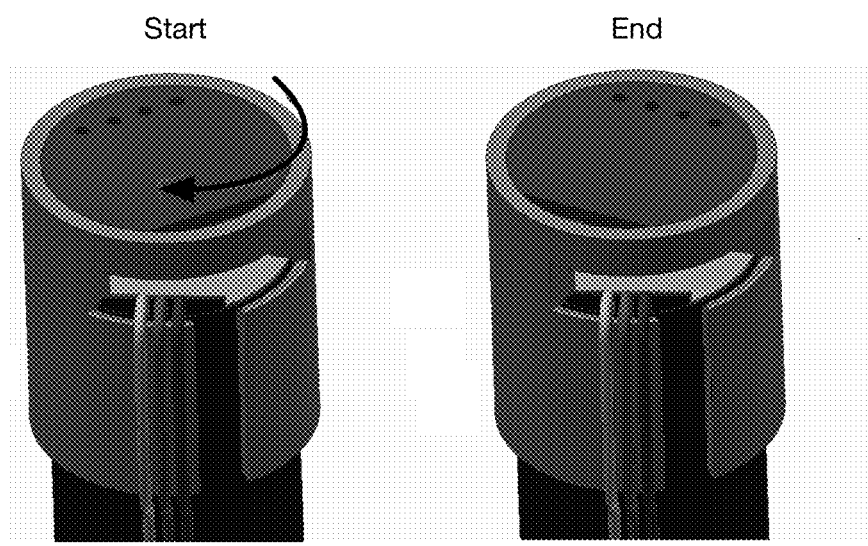

In the preferred implementation for a prosthetic hand, wherein the motor and the encoder are fixed together in a housing; the encoder may be rotated along the rotor axis to minimize the rotor offset. FIG. 12 shows a picture of how the encoder may be rotated in either direction for minimizing the rotor offset S114. In this implementation, the housing may additionally enable different increment size rotations for more customized calibration, i.e. rough adjustments, and fine adjustments.

In calibrating the sensored brushless motor S110, blocks S112 and S114 preferably function in complement together. That is, measuring rotational actuation of the rotor in two opposing directions S112 may be implemented after every incremental minimizing the rotor offset S114. In this manner, the offset is adjusted and measured repeatedly, until the offset is minimized to below the desired threshold.

Block S120, which includes embedding the motor between a first component and a second component of a prosthetic assembly, functions in enabling actuation between the first component and the second component. Embedding a motor between a first component and a second component S120 preferably includes fastening the motor within the prosthetic assembly, and connecting the sensored brushless motor to an actuating mechanism (e.g. a 4-bar linkage).

For the variation of a prosthetic hand, embedding the motor between a first component and a second component S120 may include embedding the motor components in the prosthetic hand base. Additionally, or alternatively, some motor components may be embedded in the prosthetic fingers, finger joints, or in any other prosthetic component. In one preferred implementation of this variation, wherein the motor and motor components are encased in a housing, block S120 includes connecting, or embedding the housing into the hand base. Preferably, embedding the housing in the hand base is performed for each finger of the prosthetic hand. Preferably for each prosthetic finger, the housing is embedded in proximity of the prosthetic finger such that the motor may be connected to a linkage mechanism to actuate the finger. Encasing the motor in a housing and then embedding the housing into the hand base may enable an easy way to install, remove, or replace motor components efficiently from the hand base.

Block S130, which includes controlling the motor through a field oriented control mode, functions to enable smooth full speed range functionality of the brushless motor. Field oriented control (FOC) may additionally reduce the brushless motor power consumption. Controlling the motor through a field oriented control mode S130 includes calculating two stator currents of the brushless motor, a torque component and a magnetic flux component, and implementing controllers to maintain the two stator currents at their corresponding reference values, which are generated by a central controller to reach a given finger position.

In preferred variations for a prosthetic hand with six sensored brushless motors, block S130 may be implemented individually for each motor (i.e. finger, or finger component) or may be implemented simultaneously for multiple motors (e.g. for hand gripping motions). Preferably, each motor has a distinct FOC controller, wherein each FOC controller is positioned on a single printed circuit board (PCB) within the hand base. Alternatively, the FOC controllers may be positioned in a separate housing, positioned on their associated motor, or in some other desired region within proximity of the associated motor (e.g. prosthetic finger).

In preferred variations for a prosthetic hand, the control mode may be implemented such that a user may actuate prosthetic components (i.e. prosthetic fingers) as desired for "hand activity". Thus, in preferred variations, the user may have a circuitry enabled to activate block S130 as desired. In one implementation, user muscle_signals may be picked up by electromyographic control inputs connected to the user, thereby initiating direct control of single or groups of motors.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A prosthetic assembly system comprising:
a prosthetic hand, comprising: a hand base, and a set of prosthetic fingers; and
a set of actuating systems, wherein each actuating system connects a prosthetic finger to the hand base and provides locomotion for actuation of the prosthetic finger with respect to the hand base, and each actuating system comprises:
a linkage that mechanically couples the prosthetic finger to the hand base, and
a sensored brushless motor, comprising a brushless motor, a field oriented control (FOC) control system, a rotary encoder, and a gearbox.

2. The system of claim 1, wherein the rotary encoder is tunneling magnetoresistance (TMR) sensor.

3. The system of claim 2, wherein the brushless motor further comprises a disk magnet situated on the back shaft of the brushless motor, and the TMR sensor is axially calibrated to the brushless motor along the back shaft and positioned such that the TMR sensor is proximal to the disk magnet with a defined gap between the TMR sensor and the disk magnet.

4. The system of claim 1, wherein the set of prosthetic fingers comprises five prosthetic fingers.

5. The system of claim 4, wherein one prosthetic finger from the set of prosthetic fingers is a thumb prosthetic finger, comprising two thumb components; wherein one actuating system couples to each thumb component.

6. The system of claim 1, wherein the sensored brushless motor for each prosthetic finger is identically calibrated, such that each brushless motor is calibrated to its respective rotary encoder to the same initial position, such that the calibration for all prosthetic fingers is synchronized.

7. The system of claim 6, wherein any prosthetic finger from the set of prosthetic fingers is hot-swappable, such that it may be removed and replaced with a new prosthetic finger without any additional calibrations.

8. The system of claim 1, wherein all FOC control systems from the set of actuating systems are implemented on a single printed circuit board positioned in the prosthetic hand base.

9. The system of claim 1, wherein the gearbox comprises a worm drive gearbox.

10. The system of claim 1, wherein the linkage comprises a compliant 4-bar linkage.

11. The system of claim 1, wherein the system further comprises a control input, controllably coupled to sensored brushless motors configured to perform simultaneous and independent actuation of the sensored brushless motors.

12. The system of claim 1, wherein the system further comprises a set of sensored brushless motor housings, wherein for each sensored brushless motor, the brushless motor and the rotary encoder are encased in the sensored brushless motor housings; and wherein each sensored brushless motor housing is positioned within the prosthetic hand base.

13. The system of claim 12, wherein each sensored brushless motor housing is removable from the prosthetic hand base.

14. A method for implementing brushless motors with a prosthetic assembly for a prosthetic hand comprising:
integrating an encoder with a brushless motor, comprising:
fixing a diametrically magnetized magnet to the motor rotor, and mounting an encoder above the magnet, such that the encoder is axially aligned with the motor;

calibrating the brushless motor with the encoder;

embedding the motor between a first prosthetic component and a second prosthetic component, wherein the first prosthetic component comprises a hand base and the second prosthetic component comprises a prosthetic finger; and controlling the motor through a field oriented control (FOC) mode.

15. The method of claim 14, wherein calibrating the sensored brushless motor comprises:

measuring a rotational actuation of the rotor in two opposing directions, thereby determining a rotor offset, wherein the offset comprises the difference in the measured rotational actuations of the two opposing directions, and minimizing the rotor offset, comprising reducing the rotor offset such that it is below a desired threshold.

16. The method of claim 15, wherein measuring a rotational actuation of the rotor in two opposing directions comprises:

actuating the motor in one direction with a fixed amount of power and measuring the average rotor speed of the motor during the entire actuation, and actuating the motor in the opposite direction with the fixed amount of power and measuring the average rotor speed of the motor during the entire actuation.

17. The method of claim 15, wherein measuring a rotational actuation of the rotor in two opposing directions comprises actuating the motor in one direction with a fixed amount of power and measuring the angular displacement of the motor during the entire actuation, and actuating the motor in the opposite direction with the fixed amount of power and measuring the angular displacement of the motor during the entire actuation.

18. The method of claim 15, wherein the sensored brushless motor is encased in a housing, and minimizing the rotor offset comprises rotating the encoder such that the rotor offset is reduced.

19. The method of claim 14, wherein the sensored brushless motor is encased in a housing and the embedding the motor between a first prosthetic component and a second prosthetic component, comprises, for each finger of the prosthetic hand, positioning the housing within the hand base in proximity of the prosthetic finger.

* * * * *